United States Patent

Mittelstadt et al.

Patent Number: 5,626,585
Date of Patent: May 6, 1997

[54] LIGATING CLIP ADVANCE

[75] Inventors: William A. Mittelstadt, Woodbury; Arthur V. Lang, Maplewood, both of Minn.

[73] Assignee: United States Surgical Corporation, Norwalk, Conn.

[21] Appl. No.: 308,084

[22] Filed: Sep. 16, 1994

[51] Int. Cl.⁶ ................................................ A61B 17/04
[52] U.S. Cl. ................................. 606/143; 227/19
[58] Field of Search ............................ 606/142, 143; 227/901, 175–180, 19

[56] References Cited

U.S. PATENT DOCUMENTS

| | | | |
|---|---|---|---|
| 3,086,208 | 4/1963 | Eby | 606/143 |
| 3,098,232 | 7/1963 | Brown | 606/143 |
| 3,638,847 | 2/1972 | Noiles | 606/142 |
| 3,899,914 | 8/1975 | Akiyama . | |
| 4,226,239 | 10/1980 | Polk et al. . | |
| 4,296,751 | 10/1981 | Blake, III et al. | 606/143 |
| 4,393,883 | 7/1983 | Smyth et al. . | |
| 4,430,997 | 2/1984 | DiGiovanni et al. . | |
| 4,452,357 | 6/1984 | Klieman et al. . | |
| 4,452,376 | 6/1984 | Klieman et al. . | |
| 4,470,532 | 9/1984 | Froehlich . | |
| 4,478,220 | 10/1984 | DiGiovanni et al. . | |
| 4,500,024 | 2/1985 | DiGiovanni et al. . | |
| 4,616,650 | 10/1986 | Green et al. | 606/143 |
| 4,624,254 | 11/1986 | McGarry et al. | 606/143 |
| 4,674,504 | 6/1987 | Klieman et al. . | |
| 4,850,355 | 7/1989 | Brooks et al. | 606/143 |
| 4,858,608 | 8/1989 | McQuilkin . | |
| 4,919,320 | 4/1990 | Storace . | |
| 5,030,226 | 7/1991 | Green et al. . | |
| 5,040,715 | 8/1991 | Green et al. . | |
| 5,084,057 | 1/1992 | Green et al. | 606/143 |
| 5,100,420 | 5/1992 | Green et al. . | |
| 5,151,101 | 9/1992 | Grossi et al. . | |
| 5,171,247 | 12/1992 | Hughett et al. . | |
| 5,171,249 | 12/1992 | Stefanchik et al. . | |
| 5,192,288 | 3/1993 | Thompson et al. . | |
| 5,281,230 | 1/1994 | Heidmueller . | |
| 5,282,807 | 2/1994 | Knoepfler . | |
| 5,282,808 | 2/1994 | Kovac et al. . | |
| 5,289,963 | 3/1994 | McGarry et al. . | |
| 5,300,081 | 4/1994 | Young et al. | 606/142 |
| 5,314,424 | 5/1994 | Nicholas . | |
| 5,356,064 | 10/1994 | Green et al. . | |
| 5,364,002 | 11/1994 | Green et al. . | |
| 5,382,254 | 1/1995 | McGarry et al. . | |
| 5,382,255 | 1/1995 | Castro et al. . | |

FOREIGN PATENT DOCUMENTS

0598529A2  5/1994  European Pat. Off. .
WO90/03763  4/1990  WIPO .

*Primary Examiner*—Gary Jackson

[57] ABSTRACT

A clip advance for sequentially advancing a stack of surgical clips in a surgical clip applier. The clip advance includes a longitudinally extending housing having a first channel for receiving the clips. A pusher is mounted in the housing for reciprocating longitudinal movement. The pusher has a plurality of tabs arranged to correspondingly engage and distally move respective ones of the stack of clips when said pusher is moved distally. A cam and cam surface interact to move the tabs out of longitudinal contacting alignment with the clips upon proximal movement of the pusher.

18 Claims, 4 Drawing Sheets

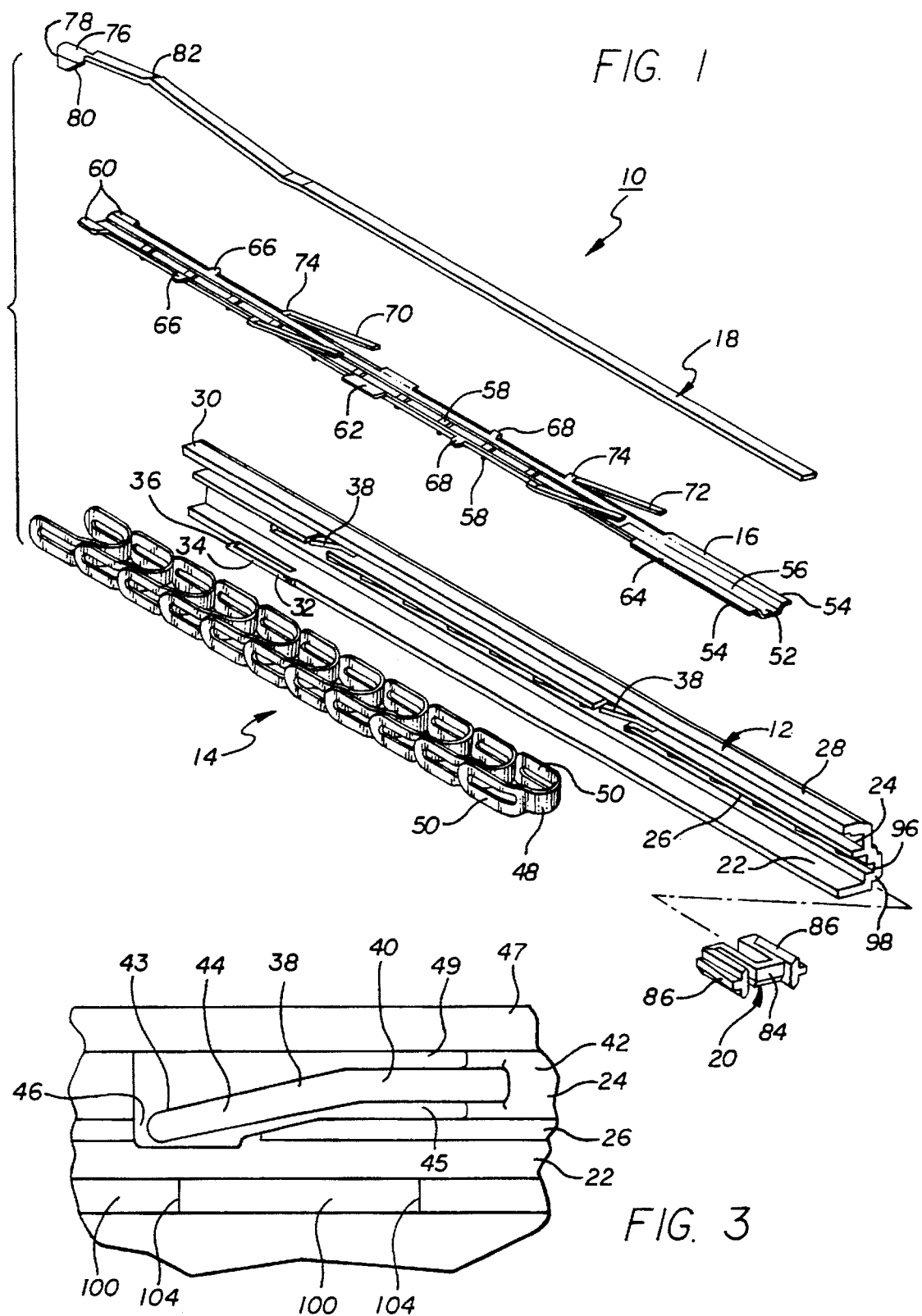

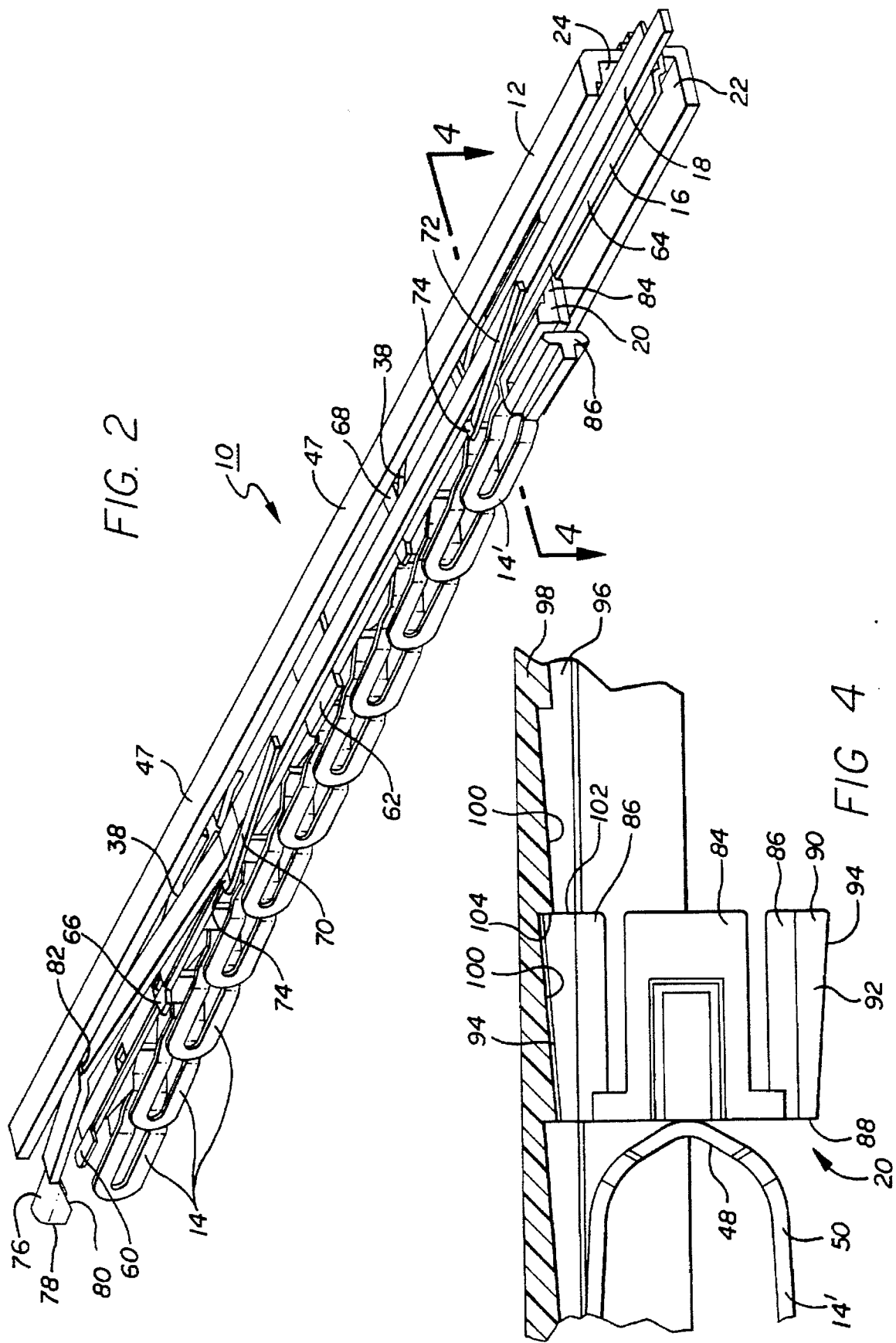

LIGATING CLIP ADVANCE

The present invention relates generally to an apparatus for sequentially advancing a plurality of clips that are used to occlude blood vessels, body tissues or organs in surgical procedures, such as laparoscopic surgical procedures, and more particularly, to an apparatus that individually engages and supports each clip during advancement.

BACKGROUND OF THE INVENTION

Surgical procedures frequently require the ligation of blood vessels, severed tissues or other organs. For this purpose, it is well known to use surgical clip appliers that advance and clamp a clip to the selected vessel, tissue or organ. See, e.g., U.S. Pat. Nos. 5,084,057, 4,616,650 and 3,086,208. Because the surgeon will typically apply many clips during the course of an operation, it has been preferred that these clip appliers contain a plurality of automatically advancing clips. Accordingly, an advancing mechanism that feeds the clips one at a time into the clamping mechanism has been necessary.

In the patents referred to above, the clips are arranged sequentially along a longitudinal axis of the clip applier. A spring is located behind the proximal-most clip and is biased to urge all the clips distally. Using the spring to advance the clips, however, is unreliable because the spring force can cause the clips to move forward with excessive force, resulting in the clips frictionally jamming against each other or getting wedged within the clip applier. Alternatively, if the frictional load on the clips is greater than the applied spring force, there will be no advancement. Also, it is possible that more than one clip at a time may advance into the clamping mechanism.

U.S. Pat. Nos. 4,452,376 and 3,899,914 disclose clip appliers wherein the clips are mechanically advanced by the operator who actuates a push bar that engages the proximal-most clip, pushing all the clips forward. While the push bar gives the operator more direct control over advancement of the clips, there still exists the problems of clip jamming and improper feeding because the clips are not visible to the operator, making it difficult to determine whether excessive force is being applied during advancement. U.S. Pat. No. 4,452,376 also describes a pawl configured to conform to the bail portion of the proximal-most clip that prevents the clips from moving proximally after advancement. The pawl, however, relies only on frictional forces to prevent rearward motion of the clips, which in some instances may be inadequate to hold the clips in place.

In another type of clip applier, the plurality of clips are advanced by a feed ratchet and a backstop ratchet. Teeth are stamped out of the ratchet bodies to contact each clip individually. Feeding occurs through reciprocating movement of the feed ratchet relative to the backstop ratchet. During clip advancement, the feed ratchet teeth push the clips forward and the backstop ratchet teeth flex out of the way as the clips pass by. When the feed ratchet is pulled back and reset, the backstop ratchet teeth prevent the clips from moving backward and the feed ratchet teeth flex out of the way as they pass over the clips. For additional details of this type of clip advance, see U.S. Pat. Nos. 4,624,254, 4,500,024, 4,452,357 and 4,430,997.

The ratchet type of clip advance reduces the problem of clip jamming because each clip is individually engaged by the teeth of the feed and backstop ratchets. The mechanism, however, does have its disadvantages. For example, the teeth themselves may become jammed during flexing, which could result in improper advancement or a failure to advance the clips. Additionally, if the teeth do not retain sufficient resiliency, they may fail to properly engage the clips during advancement or may fail to prevent their proximal movement after advancement.

In another type of clip advance, the clips are attached to a moveable belt structure having retainers that engage each individual clip, U.S. Pat. No. 5,192,288. In this device, however, the belt structure and its actuation adds an additional element of complexity to the overall design.

Accordingly, it should be appreciated that there is still a need for an improved clip applier that positively engages and advances a plurality of clips, without jamming or misfiring. Such a clip advance should also have a simple and effective construction and be easy to use.

SUMMARY OF THE INVENTION

The present invention is embodied in a clip advance for a multi-fire clip applicator. The clip advance positively advances each clip in the clip stack, thereby reducing the possibility of misfiring or jamming by wedging or friction. The clip advance also has a simple and effective construction and is easy to use.

The clip advance includes a longitudinally extending housing having a first channel for receiving a stack of surgical clips. A pusher is mounted in the housing for reciprocating longitudinal movement adjacent the plurality of clips. The pusher includes a plurality of tabs arranged to correspondingly engage and distally move respective ones of the plurality of clips when the pusher is moved distally. The tabs need not be flexible or resilient as in prior art devices. Accordingly, an advantage of the present invention is that the tabs are not likely to become jammed or wedged during clip advancement.

A feature of the present invention is that the pusher and housing are provided with a mechanism that, upon proximal movement of the pusher, lifts the tabs out of longitudinal contacting alignment with the clips. This permits the pusher to be pulled back and reset to engage the next clips in sequence. In a preferred embodiment, the mechanism for disengaging the tabs from the clips includes a cantilever ramp fixed to the housing and a transversely extending knob on the pusher that is in longitudinally contacting alignment with the cantilever ramp. Upon distal movement of the pusher, i.e., clip advancement, the knob engages and deflects the cantilever ramp out of the way as the knob passes by. Upon proximal movement of the pusher, i.e., resetting, the knob rides up the cantilever ramp, lifting the tabs out of alignment with the clips until the tabs are pulled back to a location where they can engage the next clips in sequence.

Another feature of the present invention is a biasing member that returns the tabs into contacting longitudinal alignment with the clips upon proximal disengagement of the knob from the cantilever ramp. In the preferred embodiment, the biasing member is a leaf spring fixed to the reciprocating pusher that engages an upper wall of the housing such that the upper wall applies a biasing force to the pusher urging the tabs back into contacting longitudinal alignment with the clips.

An additional feature of the present invention is a backstop located adjacent the proximal-most clip in the stack of clips. The backstop includes a deflectable wing that engages a ratcheting surface of the housing. Distal movement of the backstop relative to the ratcheting surface alternately flexes the wing inward as the wing moves along the ratchet surface, then releases the wing after movement of approximately one clip length. The wing then interfaces with a back wall of the ratcheting surface to prevent proximal movement, thus supporting the clips in their new position.

Another feature of the present invention is a staging bar mounted to the reciprocating pusher. The staging bar has a head at its distal end for engaging a distal-most clip in the first channel of the housing and advancing the clip into the clamping mechanism. The head of the staging bar also has a proximal ramp surface configured to ride over the distal-most clip upon proximal movement of the staging bar. The staging bar has a bend located proximally of the head that engages the housing in such a manner as to bias the head toward the clip.

A further feature of the invention is a distally extending cantilever arm at the distal end of the housing. The cantilever arm has a hook at its distal end in contacting longitudinal alignment with the clips to hold the clip stack back from gravity.

Other features and advantages of the present invention will become apparent from the following description of the preferred embodiment, taken in conjunction with the accompanying drawings, which illustrate, by was of example, the principles of the invention.

BRIEF DESCRIPTION OF THE DRAWINGS

FIG. 1 is an exploded perspective view of a clip advance according to the present invention.

FIG. 2 is an assembled perspective view of a clip advance of FIG. 1, showing the reciprocating pusher in its distal-most position.

FIG. 3 is an enlarged side view of a portion of the housing of the clip advance in FIG. 1.

FIG. 4 is a sectional plan view taken along line 4—4 of FIG. 3.

DETAILED DESCRIPTION OF THE PREFERRED EMBODIMENT

Figure 5A:
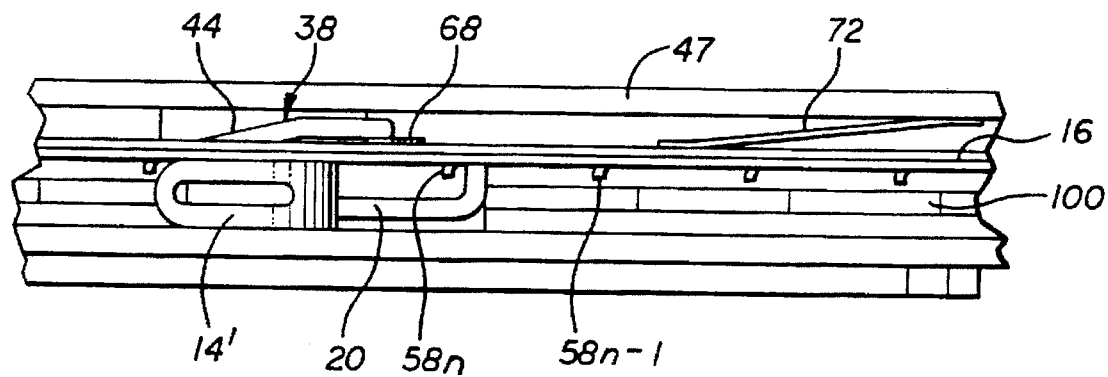
FIGS. 5A–5F are sectional side views of the assembled clip advance of FIG. 2, showing the reciprocating pusher in various stages of operation.

A clip advance 10 according to the present invention is shown in FIGS. 1 and 2. The clip advance 10 includes a housing 12, a plurality of clips 14, a reciprocating pusher 16, a staging bar 18 and a backstop 20.

The housing 12 is a clam shell type have two symmetrical halves, only one-half of which is shown. The housing is preferably molded and made of polycarbonate or other suitable material. The housing extends longitudinally and defines two longitudinally extending channels, a lower channel 22 and an upper channel 24. The lower and upper channels are separated by a common wall 26. The lower channel is configured to receive the plurality of clips 14. The upper channel is configured to receive the reciprocating pusher 16 and the staging bar 18.

The housing has a proximal end 28 and a distal end 30. A detent 32 is formed at the distal end 30 of the housing to hold the clip stack back from gravity. The detent includes a distally extending cantilever arm 34 with an inwardly extending hook 36 at the free end of the cantilever arm 34. The hook 36 is configured to engage the distal-most clip prior to its advancement into a clamping mechanism (not shown). The cantilever arm is resilient to flex out of the way when a sufficient distally directed force is applied to the distal-most clip, then, after the clip passes by, the arm returns to its unflexed position to stop the remaining clips in the stack from advancing forward.

With reference also to FIG. 3, the upper channel 24 of the housing is interrupted by one or more cantilever ramps 38, which may be formed into the housing at the time of molding. The cantilever ramps 38 have a proximal portion 40 fixed to a sidewall 42 of the upper channel 24 and a distal ramp portion 44 defining a ramp or cam surface 43. The proximal portion 40 extends longitudinally and is spaced from the common wall 26 to form a passage 45. The proximal portion is also spaced from an upper wall 47 of the upper channel 24 to form a passage 49. The distal ramp portion 44 extends toward the lower channel 22 from the proximal portion 40. A cutout 46 is provided in the common wall 26 to permit the ramp portion 44 to extend into the lower channel. The cantilever ramps 38 are sufficiently resilient to flex transversely, as will be described in more detail below.

The clips 14 are preferably each U-shaped having a closed end 48 and two legs 50. The clips are arranged in sequential alignment in the lower channel 22 with their legs 50 pointing distally.

The reciprocating pusher 16 is a longitudinally extending member located in the upper channel 24 of the housing 12. In the preferred embodiment, the reciprocating pusher includes a longitudinally extending central portion 52 and two outer support portions 54. The central portion is lower than the support portions to define a recess 56 for locating the staging bar 18.

Tabs 58 are punched out longitudinally along the central portion of the reciprocating pusher 16 (see also FIG. 5A). The tabs extend into the lower channel 22 and are spaced so that each tab engages a corresponding clip 14. The length of the tabs are sufficient to engage the closed ends of the clips. The tabs are also sufficiently rigid to apply a distally directed force to the clips in order to advance them forward.

The support portions 54 of the reciprocating pusher are not continuous for the full length of the pusher. They do, however, have sufficient length to support the pusher on the common wall 26 between the upper and lower channels. For example, the support portions may be broken into three sections, such as distal sections 60, mid sections 62 and proximal sections 64. Between the distal and mid sections 60, 62 is a first pair of transversely extending cams or knobs 66. Similarly, between the mid and proximal sections 62, 64 is a second pair of transversely extending cams or knobs 68. When the clip advance is assembled with the reciprocating pusher in the housing, the knobs 66, 68 are located adjacent the cantilever ramps 38. The knobs are sized to pass through the passages 45 between the cantilever ramps 38 and the common wall 26 and to pass through the passages 49 between the cantilever ramp and the upper wall 47 (see also FIG. 3). The interaction between the knobs and the cantilever ramps will be described in more detail below.

Also stamped out of the reciprocating pusher 16 are a first set of leaf springs 70 and a second set of leaf springs 72. Preferably, the leaf springs are stamped such that there distal ends 74 remain fixed to the reciprocating pusher. After stamping, the leaf springs are bent upwardly such that they apply a biasing force against the upper wall 47 of the housing, urging the reciprocating pusher down into engagement with the common wall 26. The leaf springs 70, 72 are located in the assembled clip advance such that they do not contact the cantilevered ramps 38 during the back and forth movement of the reciprocating pusher.

Staging bar 18 is another longitudinally extending member that is preferably seated in the recess 56 of the reciprocating pusher. The staging bar includes a distal end defining a head 76 having a distal pushing surface 78 and a proximal ramp surface 80. The pushing surface 78 extends downwardly into the lower channel 22 to engage the distal-most clip and advance it into the clamping mechanism (not shown). When the staging bar is pulled back, the proximal ramp surface causes the head to rise up and over the next clip in sequence to be advanced.

The staging bar also includes a bend 82 located proximally of the head 76. The bend 82 in the staging bar engages the upper wall 47 of the housing and applies a biasing force that urges the head 76 of the staging bar into the lower channel 22 to ensure engagement between the head of the staging bar and the clip to be advanced into the clamping mechanism.

The backstop 20 is located in the lower channel 22 of the housing. Preferably, the backstop includes a U-shaped midsection 84 and two lateral wings 86. With reference also to FIG. 4, distal ends 88 of the lateral wings 86 are fixed to the U-shaped midsection 84. Proximal ends 90 of the lateral wings are unattached so that they are permitted to flex toward the U-shaped midsection. Each lateral wing 86 includes a generally longitudinally extending lock portion 92 having a beveled surface 94. When the clip advance is assembled, the lock portions 92 are located in longitudinally extending grooves 96 located in a sidewall 98 of the lower channel 22 (see also FIG. 1).

The sidewall 98 includes ratcheting surfaces 100. The backstop 20 is located in the lower channel 22 such that the beveled surfaces 94 of the lateral wings operatively engage the ratcheting surfaces 100. It will be appreciated that as the backstop is moved distally, the lateral wings 86 will be deflected inwardly by the ratcheting surfaces 100 toward the U-shaped midsection 84. Then, the wings will resiliently deflect back to their original position as the backstop reaches its next position in sequence. A rear surface 102 of the wings 86 engages a back wall 104 of the ratcheting surface 100 to prevent backward movement of the backstop after each advancement.

The clip advance is assembled by placing the clips 14 in sequential alignment in the lower channel 22 of the housing 12. The backstop 20 is located proximally adjacent to a proximal-most clip 14'. The staging bar 18 is located in the recess 56 of the reciprocating pusher 16 and the combined unit is placed in the upper channel 24 of the housing with the tabs 58 of the reciprocating pusher in longitudinally contacting alignment with their respective clips 14. One tab $58_{n-1}$ of the reciprocating pusher is also placed proximally of the U-shaped midsection 84 of the backstop for moving the backstop distally with the clips (see FIGS. 5A–5F).

The assembled clip advance may be used with a conventional handle having an actuating member (not shown) that engages the proximal ends of the reciprocating pusher 16 and/or the staging bar 18 for proximal and distal movement. In the preferred embodiment, the actuating member is fixed to the staging bar. A pin (not shown) may be used to connect the staging bar to the reciprocating pusher. Since the staging bar may have a greater distance to travel in order to load a clip into the clamping mechanism, the pin may be located in a slot (not shown) in the reciprocating pusher to delay the interface of the staging bar and the reciprocating pusher. A conventional clamping mechanism (not shown) such as a pair of jaws and a moveable channel for closing the jaws may be located at the distal end of the device for receiving and clamping the individual clips. Those skilled in the art will appreciate that various handles and clamping mechanisms may be used with the clip advance of the present invention. Therefore, it is not intended that the present invention be limited to any particular handle or clamping mechanism.

With reference to FIGS. 5A–5F, the operation of the clip advance will now be described. In these figures, all but one clip 14' has been omitted for clarity.

In FIG. 5A, the reciprocating pusher 16 is shown in its proximal most position with the knob 68 located proximally of the cantilever ramp 38. In this position, the tabs $58_{n-1, n, n+1}, \ldots$ of the reciprocating pusher are not in engagement with the clips 14 or the backstop 20. Tab $58_n$ fits within the U-shaped mid section 84 of the backstop 20 (see also FIG. 4). Similarly, the tabs located distally of tab $58_n$ fit between the legs of the respective clips 14. The distance between the tabs and the clips in the start position may be adjusted to accommodate the extra distance that may be traveled by the staging bar for pushing the distalmost clip into the jaws of the device.

Figure 5B:
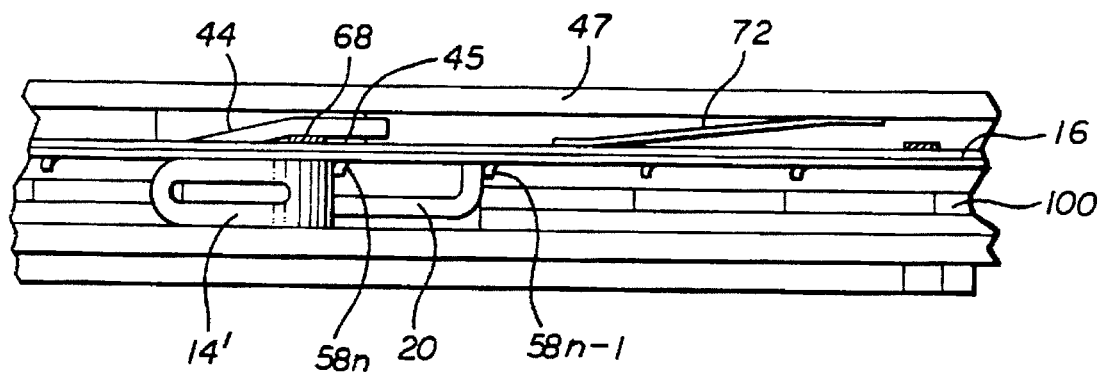
Figure 5C:
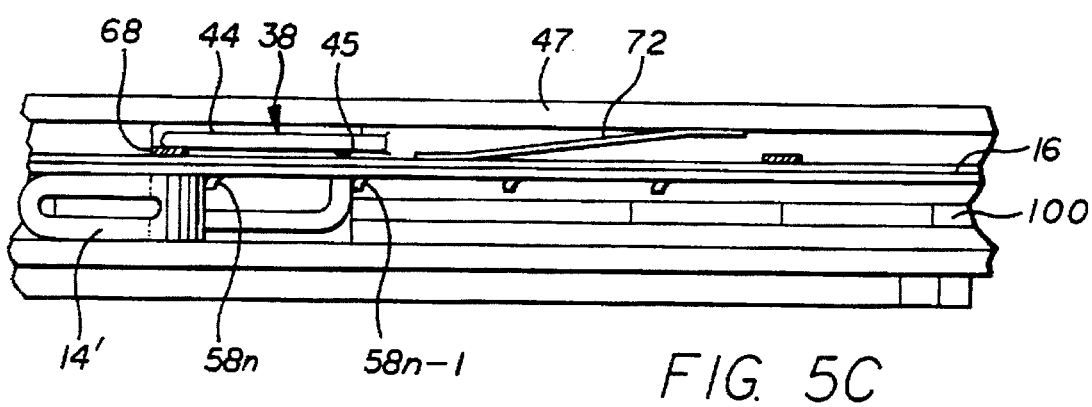
Figure 5D:
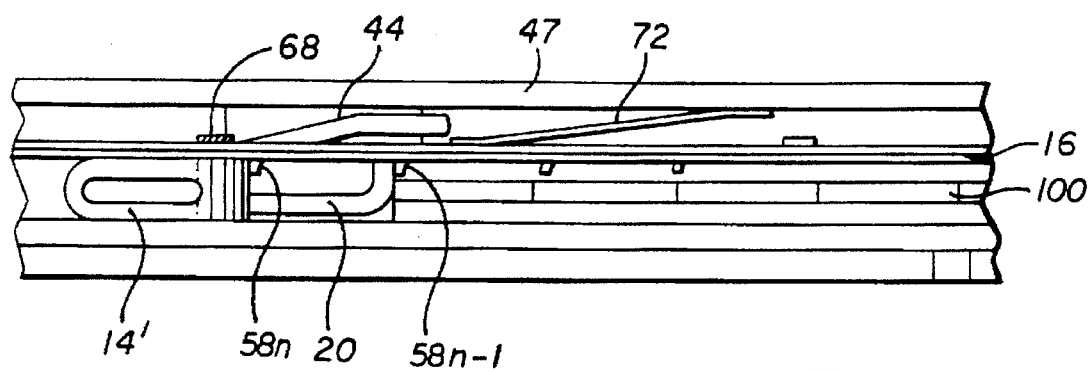

Upon actuation of the handle by an operator, the tabs 58 are advanced into engagement with the clips 14 and the backstop 20 (FIG. 5B). Further forward movement of the reciprocating pusher by actuation of the handle results in forward movement of the clips and backstop with each clip being individually engaged by its respective tab. Knob 68 also enters passage 45 between the cantilever ramp 38 and the common wall 26. In FIG. 5C, the knob 68 has advanced into engagement with the distal ramp portion 44 of the cantilever ramp, deflecting it upward as the knob passes through passage 45. In FIG. 5D, the knob has traveled completely past the cantilever ramp, which returns to its unflexed position.

During the movement shown in FIGS. 5A–5D, the reciprocating pusher advances each clip and the backstop forward until a distance of approximately one clip length is traveled. While the backstop is being pushed forward, the lateral wings 86 of the backstop are deflected inward by the ratcheting surfaces 100 on the side 98 of the housing. After one clip length is traveled, the lateral wings snap back into their unflexed condition, which supports the clips in their new position. Although not shown, the staging bar 18 has pushed the distal-most clip past the detent 32 into the clamping mechanism.

Figure 5E:
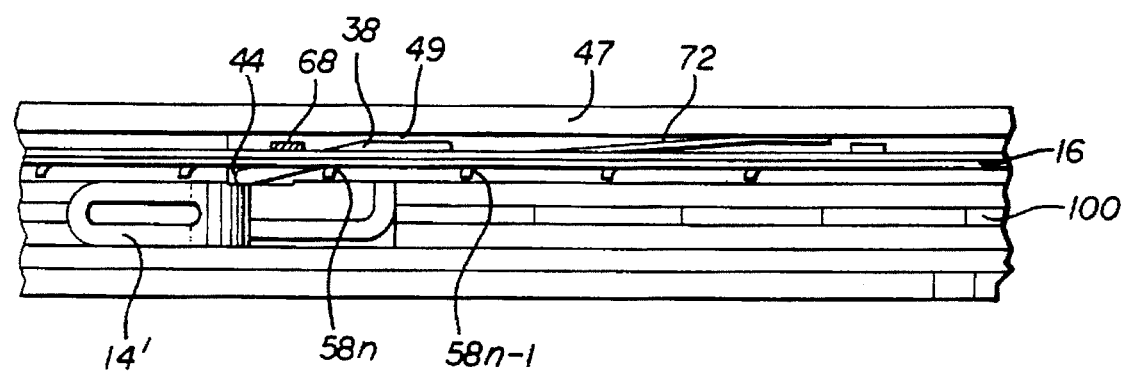
Figure 5F:
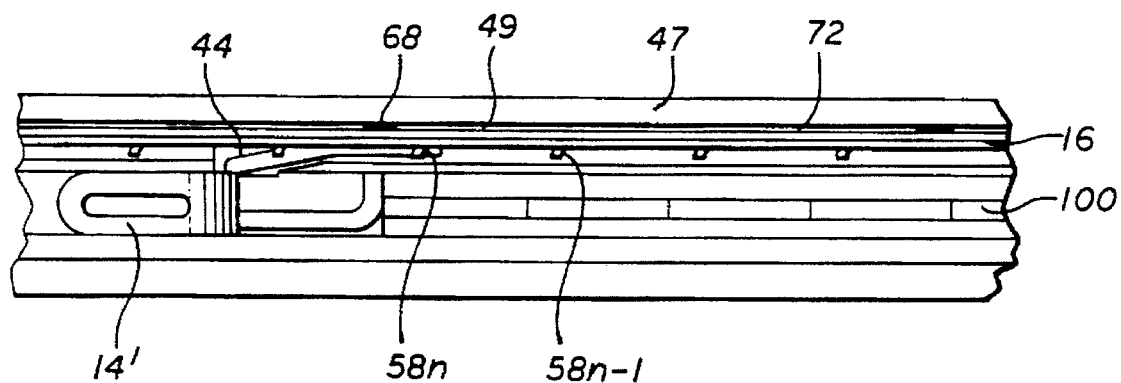

With reference to FIG. 5E, the operator has begun to release the actuator and the reciprocating pusher 16 begins to retract. The knob 68 interfaces with the cantilever ramp 38 of the housing and begins to ride up the ramp portion 44. Since the ramp is supported beneath it by the side wall, the reciprocating pusher is driven upward and the support spring 72 is deformed. This lifts the tabs 58 above the clips 14 and the backstop 20. During the return stroke, knob 68 travels through passage 49 between the cantilever ramp and the upper wall 47 of the housing (see FIG. 5F). At the end of the return motion, the knob 68 leaves the cantilever ramp and the support spring 72 returns the reciprocating pusher to its original position (see FIG. 5A). Also, during the return stroke, the staging bar 18 interfaces with a new distal-most clip to be advanced into the clamping mechanism.

It should be appreciated from the foregoing description that the present invention provides a clip advance that positively advances a stack of clips in such a manner as to substantially reduce or eliminate jamming or misfiring. In particular, each clip is individually supported and advanced by a respective tab. A mechanism is provided to disengage the tabs from the clips during resetting so that the tabs can be pulled back to reengage the next clips in sequence. The present invention also includes an improved backstop to prevent the clips from moving rearward after advancement.

Although the invention has been described in detail with reference only to the preferred embodiment, those having ordinary skill in the art will appreciate that various modifications can be made without departing from the invention. For example, an alternative embodiment would place the cantilever ramps on the reciprocating pusher and the knobs into the sidewall of the housing. Accordingly, the invention is defined with reference to the following claims.

What is claimed is:

1. A surgical clip applier for applying a plurality of surgical clips comprising a clip advance for sequentially advancing the plurality of surgical clips, the clip advance comprising:

a longitudinally extending housing having a first channel for receiving the plurality of surgical clips;

a pusher, and means mounting said pusher in the housing for reciprocating longitudinal movement adjacent the plurality of clips, the pusher having a plurality of tabs arranged to correspondingly engage and distally move respective ones of the plurality of clips when said pusher is moved distally;

wherein one of said pusher and housing has a cam and the other of said pusher and housing has a cam surface, the cam and the cam surface configured and arranged relative to each other such that, upon proximal movement of the pusher, the cam and the cam surface interact to move the tabs out of longitudinal contacting alignment with the clips.

2. A clip applier of claim 1, wherein the cam surface is on a deflectable member and the cam is rigid.

3. A clip applier of claim 2, wherein the deflectable member is a longitudinally extending cantilever ramp that is fixed at its proximal end to the housing and wherein the cam is a transversely extending knob on the pusher that is in longitudinally contacting alignment with the cantilever ramp.

4. A clip applier of claim 3, wherein, upon distal movement of the pusher, the knob engages and deflects the cantilever ramp out of the way as the knob passes by the cantilever ramp, and wherein, upon proximal movement of the pusher, the knob rides along the cantilever ramp, lifting the tabs of the pusher out of alignment with the clips.

5. A clip applier of claim 4, further comprising a biasing member that returns the tabs of the pusher into contacting longitudinal alignment with the clips upon proximal disengagement of the knob from the cantilever ramp.

6. A clip applier of claim 5, wherein the biasing member is leaf spring fixed to the pusher.

7. A clip applier of claim 1, wherein the first channel of the housing defines a ratchet surface and wherein the clip advance further comprises a backstop located in the first channel of the housing, the backstop having a deflectable wing in engagement with the ratchet surface such that distal movement of the backstop causes the wing to alternately flex inward as the wing moves along the ratchet surface and then flex outward after moving approximately one clip length.

8. A clip applier of claim 1, further comprising a staging bar mounted to the reciprocating pusher, the staging bar having a head at its distal end for engaging a distal-most clip in the first channel of the housing.

9. A clip applier of claim 8, wherein the head has a proximal ramp surface configured to ride over one of said plurality of clips upon proximal movement of the staging bar.

10. A clip applier of claim 8, wherein the staging bar has a bend located proximally of the head that engages the housing such that the housing applies a biasing force, urging the head of the staging bar toward the first channel.

11. A clip applier of claim 1, wherein the housing includes a detent at its distal end in contacting longitudinal alignment with the clips.

12. A clip applier of claim 11, wherein the detent includes a distally extending cantilever arm and a hook at the distal end of the cantilever arm, the hook in contacting longitudinal alignment with the clips.

13. A surgical clip applier for applying a plurality of surgical clips comprising a clip advance for sequentially advancing the plurality of surgical clips, the clip advance comprising:

a longitudinally extending housing having a first channel and a second channel, the first and second channels located in parallel alignment to one another, the first channel for receiving the plurality of surgical clips;

a pusher, and means mounting said pusher in the second channel of the housing for reciprocating longitudinal movement adjacent the plurality of clips, the pusher having a plurality of tabs arranged to correspondingly engage and distally move respective ones of the plurality of clips when said pusher is moved distally;

wherein one of said pusher and housing has a deflectable member and the other of said pusher and housing has a cam, the deflectable member and the cam configured and arranged relative to each other such that, upon proximal movement of the pusher, the deflectable member and the cam interact to move the tabs out of longitudinal contacting alignment with the clips without deflecting the tabs.

14. A clip applier of claim 13, wherein the deflectable member is a longitudinally extending cantilever ramp that is fixed at its proximal end to the housing and wherein the cam is a transversely extending knob on the pusher that is in longitudinally contacting alignment with the cantilever ramp.

15. A clip applier of claim 14, wherein, upon distal movement of the pusher, the knob engages and deflects the cantilever ramp out of the way as the knob passes by the cantilever ramp, and wherein, upon proximal movement of the pusher, the knob rides along the cantilever ramp, lifting the tabs of the pusher out of alignment with the clips.

16. A clip applier of claim 15, further comprising a biasing member that returns the tabs of the pusher into contacting longitudinal alignment with the clips upon proximal disengagement of the knob from the cantilever ramp.

17. A clip applier of claim 16, wherein the first channel of the housing defines a ratchet surface and wherein the clip advance further comprises a backstop located in the first channel of the housing, the backstop having a deflectable wing in engagement with the ratchet surface such that distal movement of the backstop causes the wing to alternately flex inward as the wing moves along the ratchet surface and then flex outward after moving approximately one clip length.

18. A clip applier of claim 17, further comprising a staging bar mounted to the reciprocating pusher, the staging bar having a head at its distal end for engaging a distal-most clip in the first channel of the housing.

* * * * *